United States Patent
Simonson et al.

(10) Patent No.: US 6,927,068 B2
(45) Date of Patent: Aug. 9, 2005

(54) RAPID AND NON-INVASIVE METHOD TO EVALUATE IMMUNIZATION STATUS OF A PATIENT

(75) Inventors: Lloyd G. Simonson, Spring Grove, IL (US); John R. Kelly, Rockville, MD (US)

(73) Assignee: The United States of America as represented by the Secretary of the Navy, Washington, DC (US)

(*) Notice: Subject to any disclaimer, the term of this patent is extended or adjusted under 35 U.S.C. 154(b) by 477 days.

(21) Appl. No.: 10/060,605

(22) Filed: Jan. 30, 2002

(65) Prior Publication Data

US 2003/0143636 A1 Jul. 31, 2003

(51) Int. Cl.[7] .................................. G01N 33/53
(52) U.S. Cl. ................... 436/518; 436/517; 436/514; 436/528; 436/530; 436/541; 436/810; 422/56; 422/57; 422/58; 422/59; 422/60; 435/7.1; 435/7.93; 435/7.94; 435/970; 435/252.31
(58) Field of Search ................. 436/517, 514, 436/518, 528, 530, 541, 810; 435/7.1, 7.93, 7.94, 970, 252.31; 422/56–60

(56) References Cited

U.S. PATENT DOCUMENTS

| | | |
|---|---|---|
| 4,572,834 A | 2/1986 | Stout |
| 5,103,836 A | 4/1992 | Goldstein et al. |
| 5,830,410 A | 11/1998 | Thieme et al. |
| 5,922,614 A | 7/1999 | Cesarczyk |
| 6,248,598 B1 * | 6/2001 | Bogema .................. 436/518 |

FOREIGN PATENT DOCUMENTS

GB 2 204 398 11/1988

OTHER PUBLICATIONS

Pittman et al., Anthrax vaccine: short-term safety experience in humans. Vaccine 20 (2002) 972–978.*

Brachman, P. S. (1970) Anthrax. *Ann. N Y Acad. Sci.* 174, 577–582.

Cullum, M., Lininger, Linda A., Schade, Sylvia Z., Cope, Stanton E., Ragain, James C., and Simonson, Lloyd G. (2003) *Diagnosis of Militarily Relevant Diseases Using Oral Fluid and Saliva Antibodies: Fluorescence Polarization Immunoassay.* In vol. 168, No. 11, pp. 915–921.

(Continued)

*Primary Examiner*—Bao-Thuy L. Nguyen
(74) *Attorney, Agent, or Firm*—Joseph K. Hemby, Jr.

(57) ABSTRACT

An assay method and kit for detecting the presence of a predesignated, target IgG antibody in a sample selected from one or more patient bodily fluids. The method comprises the following steps: (a) contacting the sample of one or more patient bodily fluids with a membrane-bound recombinant protective antigen to bind to the target IgG antibody in the sample; (b) previously, simultaneously or subsequently to step (a), binding the protective antigen (PA) with a conjugated label producing a detectable signal; and (c) detecting the signal whereby the presence of the target IgG antibody is determined in the sample by the intensity of the signal. The method can further comprise the step of evaluating immunization status of the patient from whom the sample came by comparing the signal or lack thereof with immunizations previously received by the patient. In a preferred embodiment, the recombinant protective antigen (PA) specifically binds to anthrax protective antigen-specific IgG antibodies. Preferably, the immunoassay of the present invention comprises a lateral-flow assay comprising a membrane, a conjugated label pad, and a recombinant protective antigen (PA) bound to the membrane.

9 Claims, 2 Drawing Sheets

OTHER PUBLICATIONS

Figure 1:
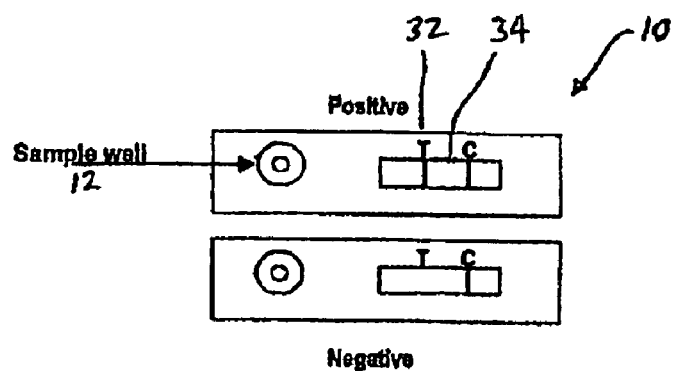

Gregory, L. (2003) *Saving Lives by Saving Time*. In vol. 20 2003, Black Issues in Higher Education. No. 10, p. 38.

Cullum, M., Lininger, Linda A., Schade, Sylvia Z., Cope, Stanton E., Ragain, James C., and Simonson, Lloyd G. (2003) *Diagnosis of Militarily Relevant Diseases Using Oral Fluid and Saliva Antibodies: Fluorescence Polarization Immunoassay*. In vol. 168, No. 11, pp. 915–921.

Stone, A., Cox, D., Valdimarsdottir, H., and Neale, J. (1987) *Secretory IgA as a Measure of Immunocompetence*. Journal of Human Stress. pp. 136–140.

Miller, K. (2001) Shots In the Dark, In Army Times pp. 14–16.

Shafazand, S., Doyle R., Ruoss, S., Weinacker, A., and Raffin, T. A. (1999) Inhalational anthrax: epidemiology, diagnosis, and management, Chest 116, 1369–1376.

Medscape.com (2001) Health experts disturbed at resurgence of anthrax in India, In vol. 2001, Medscape.

Brossier, F., Weber–levy, M., Mock, M., and J–C., S. (2000) Role of toxin functional domains in anthrax pathogenesis. Infect. Immun. 68, 1781–1786.

Singh, Y., Klimpel, K. R., Quinn, C. P., Chaudhary, V. K., and Leppla, S. H. (1991) The carboxyl–terminal end of protective antigen is required for receptor binding and anthrax toxin activity. J. Biol. Chem. 266, 15493–15497.

Brossier, F., Sirard, J.–C., Guidi–Rontani, C., Duflot, E., and Mock, M. (1999) Functional analysis of the carboxy–terminal domain of *Bacillus anthracis* protective antigen. Infect. Immun. 67, 964–967.

Little, S. F., Novak, J. M., Lowe, J. R., Leppla, S. H., Singh, Y., Klimpel, K. R., Lidgerding, B. C., and Friedlander, A. M. (1996) Characterization of lethal factor binding and cell receptor binding domains of protective antigen of *Bacillus anthracis* using monoclonal antibodies. *Microbiology* 142, 707–715.

Little, S. F., Ivins, B. E., Fellows, P. F., and Friedlander, A. M. (1997) Passive protection by polyclonal antibodies against *Bacillus anthracis* infection in guinea pigs. *Infect Immun* 65, 5171–5175.

Petosa, C., Collier, R. J., Klimpel, K. R., Leppla, S. H., and Liddington, R. C. (1997) Crystal structure of the anthrax toxin protective antigen. *Nature* 385, 833–838.

The Growing Threat of Biological Weapons. *American Scientist* 89, 28–37; Turnbull, P. C. B. (1991) Anthrax vaccines: past, present and future. *Vaccine* 9, 533–539.

Ivins, B. E., Fellows, P. F., and Nelson, G. O. (1994) Efficacy of a standard human anthrax vaccine against *Bacillus anthracis* spore challenge in guinea–pigs. *Vaccine* 12, 872–874.

Brachman, P. S., Gold, H., Plotkin, S. A., Fekety, F. R., Werrin, M., and Ingraham, N. R. (1962) Field evaluation of a human anthrax vaccine. *Am. J. Public Health* 52, 632–645.

Pittman, P. R., Mangiafico, J. A., Rossi, C. A., Cannon, T. L., Gibbs, P. H., Parker, G. W., and Friedlander, A. M. (2000) Anthrax vaccine: increasing intervals between the first two doses enhances antibody response in patients. *Vaccine* 19, 213–216.

Turnbull, P. C. B., Broster, M. G., Carman, J. A., Manchee, R. J., and Melling, J. (1986) Development of antibodies to protective antigen and lethal factor components of anthrax toxin in patients and guinea pigs and their relevance to protective immunity. *Infect. Immun.* 52, 356–363.

Little, S. F., and Knudson, G. B. (1986) Comparative efficacy of *Bacillus anthracis* live spore vaccine and protective antigen vaccine against anthrax in the guinea pig. *Infect Immun* 52, 509–512.

Ivins, B. E., Welkos, S. L., Little, S. F., Crumrine, M. H., and Nelson, G. O. (1992) Immunization against anthrax with *Bacillus anthracis* protective antigen combined with adjuvants. *Infect Immun* 60, 662–668.

Fellows, P. F., Linscott, M. K., Ivins, B. E., Pitt, M. L. M., Rossi, C. A., Gibbs, P. H., and Friedlander, A. M. (2001) Efficacy of a human anthrax vaccine in guinea pigs, rabbits, and rhesus macaques against challenge by *Bacillus anthracis* isolates of diverse geographical origin. *Vaccine* 19, 3241–3247.

Ivins, B., Fellows, P., Pitt, L., Estep, J., Farchaus, J., Friedlander, A., and Gibbs, P. (1995) Experimental anthrax vaccines: efficacy of adjuvants combined with protective antigen against an aerosol *Bacillus anthracis* spore challenge in guinea pigs. *Vaccine* 13, 1779–1784.

McBride, B. W., Mogg, A., Telfer, J. L., Lever, M. S., Miller, J., Turnbull, P. C. B., and Baillie, L. (1998) Protective efficacy of a recombinant protective antigen against *Bacillus anthracis* challenge and assessment of immunological markers. *Vaccine* 16, 810–817.

Barnard, J. P., and Friedlander, A. M. (1999) Vaccination against anthrax with attenuated recombinant strains of *Bacillus anthracis* that produce protective antigen. *Infect. Immun.* 67, 562–567.

Pitt, M. L. M., Little, S., Ivins, B. E., Fellows, P., Boles, J., Barth, J., Hewetson, J., and Friedlander, A. M. (1999) In vitro correlate of immunity in an animal model of inhalational anthrax. *J. Appl. Microbiol.* 87, 304.

Ivins, B. E., Pitt, M. L., Fellows, P. F., Farchaus, J. W., Benner, G. E., Waag, D. M., Little, S. F., Anderson, G. W. J., Gibbs, P. H., and Friedlander, A. M. (1998) Comparative efficacy of experimental anthrax vaccine candidates against inhalation anthrax in rhesus macaques. *Vaccine* 16, 1141–1148.

Zaucha, G. M., Pitt, M. L. M., Estep, J., Ivins, B. E., and Friedlander, A. M. (1998) The pathology of experimental anthrax in rabbits exposed by inhalation and subcutaneous inoculation. *Arch. Pathol. Lab. Med.* 122, 982–992.

Lehner, T. (1980) Chapter 11: Oral Immunity. In *Immunology of Oral Diseases* p. 307, Blackwell Scientific Publications, Boston, MA.

Orten, J. M., and Neuhaus, O. W. (1975) Chapter 13: Nutrition: Digestion, absorption, and energy metabolism. In *Patient Biochemistry* pp. 442–443, The C.V. Mosby Company, St. Louis, MO.

Hopp, T. P., and Woods, K. R. (1981) Prediction of protein antigenic determinants from amino acid sequences. *Proc Natl Acad Sci U S A* 78, 3824–3828.

\* cited by examiner

Figure 1. A top view of a preferred embodiment of the lateral flow test device of the present invention. A sample can be added to the sample well, with fluid membrane flow from left to right. A positive indication is shown by appearance of the test (T) line as well as the control (C). A negative indication is appearance of a control band only.

RAPID AND NON-INVASIVE METHOD TO EVALUATE IMMUNIZATION STATUS OF A PATIENT

STATEMENT REGARDING FEDERALLY SPONSORED RESEARCH OR DEVELOPMENT

The invention was made by the U.S. Navy, an agency of the United States Government. The U.S. Government has a paid-up license in this invention.

BACKGROUND OF THE INVENTION

1. Field of the Invention

The present invention relates to an immunodiagnostic assay method and kit to rapidly evaluate immunization status of a patient, or alternatively, to verify exposure to a biowarfare agent, such as anthrax, in a patient.

2. Description of the Related Art

A critical need exists for rapid, reliable, non-invasive and safe testing procedures to evaluate immunization status, such as anthrax immunization status, of a patient.

The terrorist attacks of Sep. 11, 2001 in the United States and the outbreak of anthrax in Florida, New York, Washington D.C., etc. shortly thereafter has brought the threat of biowarfare into sharp focus for the general public. Biowarfare agents have been of significant concern for the Department of Defense (DoD) for the last couple of decades in particular. Anthrax is considered one of the most dangerous of biowarfare threats because of its potency and very high mortality rate. One gram of anthrax material is estimated to give 100 million lethal doses, or is 100,000 times more lethal than the deadliest chemical warfare agent. DoD (1998) Information Paper: The Anthrax Vaccine. In Vol. 2001. Anthrax weapons are also relatively inexpensive to develop because the bacterial spores are relatively easy to obtain and can be packaged into a bomb or missile for delivery. It has been estimated that at least 10 countries in the world have, or are developing, biological warfare capability that includes anthrax. Miller, K. (2001) Shots in the Dark. In Army Times pp. 14–16.

The Persian Gulf War (1990–1991) brought the threat of this disease into sharp focus for the DoD, because Iraq was thought to have developed and stockpiled anthrax weapons. As a preventive measure, nearly all British troops and about 150,000 U.S. troops were administered anthrax vaccines for protection in the early stages of the war. To counter the growing threat to military personnel deployed overseas, the Secretary of Defense mandated in 1997 that all active duty personnel must be vaccinated for protection against possible anthrax exposure.

Although the mandatory Anthrax Vaccine Immunization Program (AVIP) was initiated in early 1998, there have been no known follow-up studies in immunized personnel to verify antibody production against the antigenic component of the anthrax toxin. As a result, DoD has sponsored research for developing countermeasures to biological warfare agents and for developing methods of verifying vaccine effectiveness. As part of the DoD Broad Agency Announcement (BAA) 99-1 released in December 1998, the Medical Biological Defense Research Program outlined the need for identification of markers of protection and assay development to assess the level of protection against biological warfare agents.

Current testing methods measure serum antibody levels in response to vaccines by time-consuming, labor-intensive processes. Highly trained laboratory personnel are needed to perform these current tests, and the instrumentation required for current tests is relatively sophisticated and expensive. While Enzyme-Linked Immunosorbent Assay (ELISA) has been the standard for measuring antibody titers, it is more problematic to perform this diagnostic test in forward-deployed regions where military personnel are at greater potential risk for anthrax toxin exposure.

The following discussion provides background on the anthrax bacteria, anthrax vaccines, animal models and anthrax strains.

Anthrax Bacteria Characterization

The Gram-positive, rod-shaped bacterium *Bacillus anthracis* is the toxic agent of anthrax infection, a natural disease endemic to grazing animals including cattle, goats and sheep. There are three forms of anthrax infection in patients: (1) cutaneous infection that occurs by dermal absorption of the bacteria through a cut or abrasion in the skin; (2) gastrointestinal infection resulting from ingestion of contaminated meat products; and (3) inhalation of anthrax spores, which is the most lethal form of exposure. The prescribed medical treatment for all forms of the disease is high doses of antibiotic, most commonly penicillin. However, bacterial resistance to third-generation cephalosporins has been documented, further thwarting attempts to quickly treat this infection. Shafazand, S., Doyle, R., Ruoss, S., Weinacker, A., and Raffin, T. A. (1999) Inhalational anthrax: epidemiology, diagnosis, and management. *Chest* 116, 1369–1376.

Fortunately, anthrax is not highly contagious among animals or patients, with infection occurring only by direct absorption of the bacteria in one of the ways listed. However, outbreaks of the disease still occur in countries that do not have active livestock vaccination programs or effective patient vaccines. Therefore, anthrax is still a danger to public health in less-developed countries such as India, where a deadly outbreak occurred in 1999–2000 in Pondicherry territory. See medscape.com (2001) Health experts disturbed at resurgence of anthrax in India. In Vol. 2001, Medscape.

*Bacillus anthracis* bacteria possess two virulence factors, the anthrax toxin and the protective capsule. The pXO1 plasmid is known to contain the specific genes for the toxin protein components, and the pXO2 plasmid encodes formation of the poly-D-glutamic acid capsule that prevents cellular phagocytic action against the bacteria. Toxins secreted by this bacterium are composed of binary combinations of three proteins: protective antigen (PA), which is only virulent when bound with either one of two additional proteins, lethal factor or edema factor. The primary antigenic protein recovered from bacteria culture filtrates is PA, an 83 kilodalton (kDa) protein encoded by the pag gene on the pXO1 plasmid of the bacterium. Edema factor (EF, 89 kDa), encoded by a separate gene on the pXO1 plasmid, is a calcium/calmodulin-dependent adenylate cyclase that stimulates cyclic adenosine monophosphate (cAMP) production resulting in inflammation, redness and soreness. Lethal factor (LF, 83 kDa), also encoded by a gene on this same plasmid, appears to be a metalloendopeptidase that cleaves the N-terminus of mitogen-activated protein kinase 1 and 2 (MAPKK1 and MAPKK2) and thereby inhibits the MAPK signal transduction pathway.

It is the PA-LF bound form of the toxin that results in serious illness or death if not promptly treated. Brossier, F., Weber-Levy, M., Mock, M., and J-C., S. (2000) Role of toxin functional domains in anthrax pathogenesis. *Infect. Immun.* 68, 1781–1786.

Actual toxic activity occurs when PA, the binding domain of anthrax toxin, recognizes and binds to cell-surface receptors. This is followed by cleavage of a 20 kDa fragment from the N-terminus by furin-like cellular proteases, leaving the membrane-bound, mature PA protein (63 kDa). Proteolytic activation of PA causes formation of a membrane-inserting heptamer that creates a channel through the cell membrane. This activation process also exposes a high affinity binding site on PA for which the other two proteins LF and EF compete. After either factor binds to PA, the protein complex then translocates through the membrane via receptor-mediated endocytosis to deliver the toxic enzymes to the cell. Once in the cytoplasm, these toxins disrupt normal cellular functions, eventually causing cell death.

Several laboratories have shown that specific critical components of the PA protein confer the toxic nature of anthrax. Singh et al. have shown that the C-terminus of PA is crucial to recognition of and binding by the host cell. Singh, Y., Klimpel, K. R., Quinn, C. P., Chaudhary, V. K., and Leppla, S. H. (1991) The carboxyl-terminal end of protective antigen is required for receptor binding and anthrax toxin activity. *J. Biol. Chem.* 266, 15493–15497.

By constructing truncations of the C-terminal domain or deletion mutants in the C-terminus loop, different laboratories were able to create a form of anthrax that is less cytotoxic or nontoxic. Singh, Y., Klimpel, K. R., Quinn, C. P., Chaudhary, V. K., and Leppla, S. H. (1991) The carboxyl-terminal end of protective antigen is required for receptor binding and anthrax toxin activity. *J. Biol. Chem.* 266, 15493–15497; and Brossier, F., Sirard, J.-C., Guidi-Rontani, C., Duflot, E., and Mock, M. (1999) Functional analysis of the carboxy-terminal domain of *Bacillus anthracis* protective antigen. *Infect. Immun.* 67, 964–967.

Another laboratory showed that pretreatment with anti-PA monoclonal antibodies prevented binding of $^{125}$I-LF or $^{125}$I-EF labeled analogs to activated PA, thereby inhibiting toxin activity. Little, S. F., Novak, J. M., Lowe, J. R., Leppla, S. H., Singh, Y., Klimpel, K. R., Lidgerding, B. C., and Friedlander, A. M. (1996) Characterization of lethal factor binding and cell receptor binding domains of protective antigen of *Bacillus anthracis* using monoclonal antibodies. *Microbiology* 142, 707–715; and Little, S. F., Ivins, B. E., Fellows, P. F., and Friedlander, A. M. (1997) Passive protection by polyclonal antibodies against *Bacillus anthracis* infection in guinea pigs. *Infect Immun* 65, 5171–5175.

Petosa demonstrated that the first, or N-terminal domain of PA, containing the protease cleavage site, is also susceptible to mutation. When point mutations were made in the amino acid sequence of this region, cleavage of the 20 kDa N-terminus did not occur and PA was not activated to expose the EF/LF binding site, resulting in no toxicity. Petosa, C., Collier, R. J., Klimpel, K. R., Leppla, S. H., and Liddington, R. C. (1997) Crystal structure of the anthrax toxin protective antigen. *Nature* 385, 833–838.

This spore-forming bacterium is also widely considered a possible weapon for biological warfare and bioterrorism because the spores are extremely stable and robust, surviving for many years in arid and semi-arid conditions. Shafazand, S., Doyle, R., Ruoss, S., Weinacker, A., and Raffin, T. A. (1999) Inhalational anthrax: epidemiology, diagnosis, and management. *Chest* 116, 1369–1376.

In the spore form, *Bacillus anthracis* may easily be dispersed over a wide area and poses a lethal challenge when inhaled. The DoD estimates that among exposed individuals, the lethal dose ($LD_{50}$) is between 8,000 and 10,000 spores. Block, S. M. (2001) The Growing Threat of Biological Weapons. *American Scientist* 89, 28–37.

Further complications result in that exposure to inhalational anthrax is not easily diagnosed because the infection initially presents with nonspecific influenza-like symptoms. The U.S. government believes that a number of countries have developed anthrax biological weapons and are capable of releasing these weapons. Concern for public safety from possible terrorist acts has led many cities to develop an emergency contingency plan outlining medical and civic responses in the event of a toxin release. The possibility of chemical or biological agent exposure may not be so unimaginable in that a 1995 terrorist release of sarin nerve gas in a crowded Tokyo subway had a devastating outcome, affecting almost 5,000 people.

Anthrax Vaccine History

In the 1870's Louis Pasteur studied the bacterium *Bacillus anthracis* in some of his earliest work in bacteriology and the germ theory of disease. Brachman, P. S. (1970) Anthrax. *Ann. NY Acad. Sci.* 174, 577–582. Robert Koch also used this bacterium in 1876 as a model in describing his postulates of germ theory. Id.

In 1881 Pasteur successfully field-tested an animal anthrax vaccine, a remarkable achievement that set the stage for significant advances in immunology and the understanding and treatment of disease. Id.; Block, S. M. (2001) The Growing Threat of Biological Weapons. *American Scientist* 89, 28–37; Tumbull, P. C. B. (1991) Anthrax vaccines: past, present and future. *Vaccine* 9, 533–539.

A serious outbreak of patient anthrax occurred in the United States around 1924 and again in the early 1930's. At that time, cutaneous and inhalation anthrax occurred at a high rate among individuals working in textile mills and animal processing plants who handled the hides and hair of infected cattle, sheep and goats both domestic and imported. This significant health risk led to the first animal anthrax vaccination program and to the development of a patient anthrax vaccine in the 1950's. As a result of the vaccination program for workers at risk, the incidence of anthrax endemic to the U.S. virtually disappeared over the next four decades. The vaccine was reformulated during the period 1957–1960 to select a strain of anthrax that produced a higher fraction of PA. A form of protein-free culture medium was also employed and aluminum hydroxide was adapted as the adjuvant. Ashford, D. A., D. V. M., M. P. H., D. Sc., and Rotz, L. D., M.D. (2000) Use of Anthrax Vaccine in the United States. In pp. 1–20, Centers for Disease Control and Prevention, Atlanta, Ga.

This vaccine was licensed for patient use in 1970 by the National Institutes of Health, and was later approved by the U.S. Food and Drug Administration (FDA). DoD (1998) Information Paper: The Anthrax Vaccine. In Vol. 2001.

In 1990, filtration-sterilization procedures in the anthrax vaccine production process were changed, resulting in higher levels of PA toxin component in the vaccine. Ivins, B. E., Fellows, P. F., and Nelson, G. O. (1994) Efficacy of a standard patient anthrax vaccine against *Bacillus anthracis* spore challenge in guinea-pigs. *Vaccine* 12, 872–874.

Current Vaccine Development

In the United States, BioPort Corporation in Lansing, Mich. exclusively produces the anthrax vaccine currently used for patients. The Anthrax Vaccine Adsorbed (AVA) vaccine is produced from the antigenic protein PA, recovered from cell-free culture filtrates of an avirulent, non-encapsulated strain of *Bacillus anthracis*. The filtrate is adsorbed onto aluminum hydroxide, an adjuvant that stimulates antibody production (humoral response) against the antigenic toxin protein. Currently, anthrax immunization involves six injections over an 18 month period, with annual boosters thereafter. The first three subcutaneous injections are given 2 weeks apart, followed by three additional injections at 6, 12 and 18 months. This immunization schedule is based upon one determined for earlier generations of anthrax vaccine and studies that examined vaccine effectiveness in animal models at that time, but additional work is needed to determine efficacy of recently developed vaccines.

Presently, there is little direct scientific evidence that patients vaccinated with AVA are protected against anthrax. The only patient study that addresses vaccine effectiveness was an epidemiological evaluation of vaccinated and unvaccinated employees in four textile mills in the 1950's and the incidence of anthrax among these at-risk workers. Brachman, P. S., Gold, H., Plotkin, S. A., Fekety, F. R., Werrin, M., and Ingraham, N. R. (1962) Field evaluation of a patient anthrax vaccine. *Am. J. Public Health* 52, 632–645.

The anthrax vaccine in use at the time predated the AVA that was reformulated for patient use around 1960. More documentation exists for vaccine protection against cutaneous anthrax, the most common form of the disease (reported to be greater than 95% of all U.S. cases (Brachman, P. S. (1970) Anthrax. *Ann. NY Acad. Sci.* 174, 577–582), with very little proof of effectiveness against the inhalation form of infection. Other indirect evidence of vaccine effectiveness was gathered in a retrospective analysis that measured patient IgG antibody titer after AVA administration in stored sera of immunized laboratory personnel. Pittman, P. R., Mangiafico, J. A., Rossi, C. A., Cannon, T. L., Gibbs, P. H., Parker, G. W., and Friedlander, A. M. (2000) Anthrax vaccine: increasing intervals between the first two doses enhances antibody response in patients. *Vaccine* 19, 213–216.

Animal Models and Anthrax Strains

Several experimental animal models have been studied to assess the effectiveness of patient AVA vaccine in the United States and of the vaccine used in the United Kingdom. However, the two vaccines differ in the *Bacillus anthracis* strain used. Historically, guinea pigs have been the primary animal model studied to evaluate vaccine effectiveness. Results of studies conducted with this model show that AVA gives variable protection when the animals are challenged intramuscularly with anthrax spores. In these studies, 0% to 100% of the immunized animals survived challenge with various spore strains. Ivins, B. E., Fellows, P. F., and Nelson, G. O. (1994) Efficacy of a standard patient anthrax vaccine against *Bacillus anthracis* spore challenge in guinea-pigs. *Vaccine* 12, 872–874; Turnbull, P. C. B., Broster, M. G., Carman, J. A., Manchee, R. J., and Melling, J. (1986) Development of antibodies to protective antigen and lethal factor components of anthrax toxin in patients and guinea pigs and their relevance to protective immunity. *Infect. Immun.* 52, 356–363; Little, S. F., and Knudson, G. B. (1986) Comparative efficacy of *Bacillus anthracis* live spore vaccine and protective antigen vaccine against anthrax in the guinea pig. *Infect Immun* 52, 509–512; Ivins, B. E., Welkos, S. L., Little, S. F., Crumrine, M. H., and Nelson, G. O. (1992) Immunization against anthrax with *Bacillus anthracis* protective antigen combined with adjuvants. *Infect Immun* 60, 662–668; and Fellows, P. F., Linscott, M. K., Ivins, B. E., Pitt, M. L. M., Rossi, C. A., Gibbs, P. H., and Friedlander, A. M. (2001) Efficacy of a patient anthrax vaccine in guinea pigs, rabbits, and rhesus macaques against challenge by *Bacillus anthracis* isolates of diverse geographical origin. *Vaccine* 19, 3241–3247.

Also, AVA did not provide good protection in the guinea pig against an aerosol spore challenge, with only 20%–26% of the animals surviving. Ivins, B., Fellows, P., Pitt, L., Estep, J., Farchaus, J., Friedlander, A., and Gibbs, P. (1995) Experimental anthrax vaccines: efficacy of adjuvants combined with protective antigen against an aerosol *Bacillus anthracis* spore challenge in guinea pigs. *Vaccine* 13, 1779–1784.

These studies, although consistent among themselves, demonstrate the tremendous variability of survival rates in this animal model when challenged with different spore strains. There may also be species-specific differences in that the guinea pig has an acute susceptibility to infection, but relative resistance to toxin effects. McBride, B. W., Mogg, A., Telfer, J. L., Lever, M. S., Miller, J., Turnbull, P. C. B., and Baillie, L. (1998) Protective efficacy of a recombinant protective antigen against *Bacillus anthracis* challenge and assessment of immunological markers. *Vaccine* 16, 810–817.

It was also proposed that this animal model may respond poorly to the AVA vaccine itself. Fellows, P. F., Linscott, M. K., Ivins, B. E., Pitt, M. L. M., Rossi, C. A., Gibbs, P. H., and Friedlander, A. M. (2001) Efficacy of a patient anthrax vaccine in guinea pigs, rabbits, and rhesus macaques against challenge by *Bacillus anthracis* isolates of diverse geographical origin. *Vaccine* 19, 3241–3247.

This observation is supported by studies in which PA vaccines with different adjuvants caused higher antibody titers against PA than AVA and seemed to confer better protection. Ivins, B. E., Welkos, S. L., Little, S. F., Crumrine, M. H., and Nelson, G. O. (1992) Immunization against anthrax with *Bacillus anthracis* protective antigen combined with adjuvants. *Infect Immun* 60, 662–668.

The original Sterne strain (pXO1$^+$, pXO2$^+$) has proven to be the most virulent in guinea pigs, while the Ames and Vollum 1B strains showed progressively decreasing levels of virulence. A few of the studies cited above employed challenges with different strains of anthrax spores, thereby introducing the possibility that the variable survival rates were due to the virulence of the spore strain. In these studies, it was shown that patient vaccine provided significantly better protection in animals challenged with Vollum or Vollum 1B spore strains than those challenged with the Ames strain (also known as a 'vaccine resistant' strain). Turnbull, P. C. B., Broster, M. G., Carman, J. A., Manchee, R. J., and Melling, J. (1986) Development of antibodies to protective antigen and lethal factor components of anthrax toxin in patients and guinea pigs and their relevance to protective immunity. *Infect. Immun.* 52, 356–363; Little, S. F., and Knudson, G. B. (1986) Comparative efficacy of *Bacillus anthracis* live spore vaccine and protective antigen vaccine against anthrax in the guinea pig. *Infect Immun* 52, 509–512; and Ivins, B. E., Fellows, P. F., and Nelson, G. O. (1994) Efficacy of a standard patient anthrax vaccine against *Bacillus anthracis* spore challenge in guinea-pigs. *Vaccine* 12, 872–874.

This suggests that virulence of the challenge anthrax strain also impacts the degree of protection provided by patient vaccines. Alternately, a study of immunization with a live Sterne spore vaccine resulted in a higher survival rate than in those animals immunized with the PA-based patient vaccine and challenged with different spore strains. Turnbull, P. C. B., Broster, M. G., Carman, J. A., Manchee, R. J., and Melling, J. (1986) Development of antibodies to protective antigen and lethal factor components of anthrax toxin in patients and guinea pigs and their relevance to protective immunity. *Infect. Immun.* 52, 356–363; Little, S. F., and Knudson, G. B. (1986) Comparative efficacy of Bacillus anthracis live spore vaccine and protective antigen vaccine against anthrax in the guinea pig. Infect Immun 52, 509–512.

In studies examining survival rates of immunized guinea pigs challenged intramuscularly with the Ames spore strain, anti-PA antibody titers were also measured and found to be an accurate predictor of survival in one study (see Barnard, J. P., and Friedlander, A. M. (1999) Vaccination against anthrax with attenuated recombinant strains of Bacillus anthracis that produce protective antigen. Infect. Immun. 67, 562–567), but not an accurate predictor in other studies. See Turnbull, P. C. B., Broster, M. G., Carman, J. A., Manchee, R. J., and Melling, J. (1986) Development of antibodies to protective antigen and lethal factor components of anthrax toxin in patients and guinea pigs and their relevance to protective immunity. Infect. Immun. 52, 356–363; Little, S. F., and Knudson, G. B. (1986) Comparative efficacy of Bacillus anthracis live spore vaccine and protective antigen vaccine against anthrax in the guinea pig. Infect Immun 52, 509–512; Ivins, B. E., Welkos, S. L., Little, S. F., Crumrine, M. H., and Nelson, G. O. (1992) Immunization against anthrax with Bacillus anthracis protective antigen combined with adjuvants. Infect Immun 60, 662–668; and Ivins, B. E., Fellows, P. F., and Nelson, G. O. (1994) Efficacy of a standard patient anthrax vaccine against Bacillus anthracis spore challenge in guinea-pigs. Vaccine 12, 872–874.

The latter studies found no significant correlation between anti-PA antibody titer and survival using patient vaccines isolated from culture filtrates. However, it should also be noted in studies conducted before 1990, the patient vaccine used was not optimized for PA expression. The type of adjuvant used also influenced the protective effect in experimental vaccines (see Ivins, B. E., Fellows, P. F., and Nelson, G. O. (1994) Efficacy of a standard patient anthrax vaccine against Bacillus anthracis spore challenge in guinea-pigs. Vaccine 12, 872–874 Ivins, B. E., Fellows, P. F., and Nelson, G. O. (1994) Efficacy of a standard patient anthrax vaccine against Bacillus anthracis spore challenge in guinea-pigs. Vaccine 12, 872–874) and affected the amount of anti-PA produced against the vaccine (see McBride, B. W., Mogg, A., Telfer, J. L., Lever, M. S., Miller, J., Turnbull, P. C. B., and Baillie, L. (1998) Protective efficacy of a recombinant protective antigen against Bacillus anthracis challenge and assessment of immunological markers. Vaccine 16, 810–817).

A recent study using rabbits supports the conclusion that antibody levels to PA after AVA immunization predicted protection in animals receiving an aerosolized Ames spore challenge. Pitt, M. L. M., Little, S., Ivins, B. E., Fellows, P., Boles, J., Barth, J., Hewetson, J., and Friedlander, A. M. (1999) In vitro correlate of immunity in an animal model of inhalational anthrax. J Appl. Microbiol. 87, 304.

A protective effect of 90% or greater was also realized in AVA-immunized rabbits challenged with a number of virulent spore strains, confirming efficacy of the vaccine in this animal model. Fellows, P. F., Linscott, M. K., Ivins, B. E., Pitt, M. L. M., Rossi, C. A., Gibbs, P. H., and Friedlander, A. M. (2001) Efficacy of a patient anthrax vaccine in guinea pigs, rabbits, and rhesus macaques against challenge by Bacillus anthracis isolates of diverse geographical origin. Vaccine 19, 3241–3247.

It is the work conducted with non-patient primates, however, that is believed to most closely predict the protection afforded patients against anthrax spore inhalation. In a study conducted with rhesus macaques immunized with patient AVA (and with other experimental vaccines using rPA, a recombinant form of PA), all vaccinated monkeys survived a subsequent aerosol challenge of lethal doses of Ames strain spores, while all control animals perished. Ivins, B. E., Pitt, M. L., Fellows, P. F., Farchaus, J. W., Benner, G. E., Waag, D. M., Little, S. F., Anderson, G. W. J., Gibbs, P. H., and Friedlander, A. M. (1998) Comparative efficacy of experimental anthrax vaccine candidates against inhalation anthrax in rhesus macaques. Vaccine 16, 1141–1148.

In a recent study in which AVA protection of guinea pigs, rabbits and rhesus macaques was evaluated, rabbits and non-patient primates showed nearly complete protection against an aerosol spore challenge. Fellows, P. F., Linscott, M. K., Ivins, B. E., Pitt, M. L. M., Rossi, C. A., Gibbs, P. H., and Friedlander, A. M. (2001) Efficacy of a patient anthrax vaccine in guinea pigs, rabbits, and rhesus macaques against challenge by Bacillus anthracis isolates of diverse geographical origin. Vaccine 19, 3241–3247.

Other laboratories have shown that vaccines containing PA derived from various recombinant plasmids are effective against aerosolized toxin exposure in nonpatient primates (see Ivins, B. E., Pitt, M. L., Fellows, P. F., Farchaus, J. W., Benner, G. E., Waag, D. M., Little, S. F., Anderson, G. W. J., Gibbs, P. H., and Friedlander, A. M. (1998) Comparative efficacy of experimental anthrax vaccine candidates against inhalation anthrax in rhesus macaques. Vaccine 16, 1141–1148) or in other animal models. See Zaucha, G. M., Pitt, M. L. M., Estep, J., Ivins, B. E., and Friedlander, A. M. (1998) The pathology of experimental anthrax in rabbits exposed by inhalation and subcutaneous inoculation. Arch. Pathol. Lab. Med. 122, 982–992; Barnard, J. P., and Friedlander, A. M. (1999) Vaccination against anthrax with attenuated recombinant strains of Bacillus anthracis that produce protective antigen. Infect. Immun. 67, 562–567; Pitt, M. L. M., Little, S., Ivins, B. E., Fellows, P., Boles, J., Barth, J., Hewetson, J., and Friedlander, A. M. (1999) In vitro correlate of immunity in an animal model of inhalational anthrax. J. Appl. Microbiol. 87, 304; and Shafazand, S., Doyle, R., Ruoss, S., Weinacker, A., and Raffin, T. A. (1999) Inhalational anthrax: epidemiology, diagnosis, and management. Chest 116, 1369–1376.

Based upon this large body of evidence, a new experimental vaccine using rPA as the antigenic component is now under development at a number of laboratories. When approved by the FDA, this new generation of anthrax vaccines will become the standard to immunize personnel at risk of exposure.

The variability of survival outcomes in animal models may be a direct effect of the differing virulence of the challenge strains and the types of vaccines used. Therefore, the results are inconclusive because vaccine efficacy in one animal model cannot be compared to the protection afforded other animals immunized with the same vaccines or challenged with the same anthrax strains. This also clearly points out the inherent difficulty in extrapolating results of anthrax vaccine protection in animals to that in patients. In the absence of any controlled patient trials of vaccine effectiveness, the best animal model is the non-patient primate. Clearly, additional work needs to be conducted with this model.

BRIEF SUMMARY OF THE INVENTION

The present invention comprises an immunodiagnostic assay method and kit to rapidly evaluate immunization status of a patient, or alternatively to verify exposure to a biowarfare agent, such as anthrax, in a patient. The method and kit of the present invention provides rapid, reliable, non-invasive and safe testing procedures.

More specifically, the present invention comprises a method for detecting the presence of a predesignated, target IgG antibody in a sample selected from one or more patient bodily fluids which comprises the following steps: (a) contacting the sample of one or more patient bodily fluids with a membrane-bound recombinant protective antigen to bind to the target IgG antibody in the sample; (b) previously, simultaneously or subsequently to step (a), binding the protective antigen with a conjugated label producing a detectable signal; and (c) detecting the signal whereby the presence of the target IgG antibody is determined in the sample by the intensity or presence of the signal.

In accordance with the present invention, the one or more bodily fluids is selected from the group consisting of saliva, oral rinse expectorant, oral fluid including oral mucosal transudate and gingival crevicular fluid, urine, sweat, tears, blood, serum, stool, gastric fluid, synovial fluid, phlegm, culture media and other clinical and laboratory specimens and samples. In a preferred embodiment of the invention, the one or more bodily fluids used in the method is saliva.

The present invention further provides the step of evaluating immunization status of the patient from whom the sample came by comparing the signal or lack thereof with immunizations previously received by the patient and in comparison to a known standard control.

In a preferred method, the recombinant protective antigen specifically binds to anthrax protective antigen-specific IgG antibodies.

The invention also provides an immunoassay kit for detecting a pre-designated target IgG antibody in a sample selected from one or more patient bodily fluids which comprises: (a) a lateral-flow assay comprising a membrane, (b) a conjugated label pad, and (c) a recombinant protective antigen bound to the membrane. In a preferred kit, the recombinant protective antigen specifically binds to anthrax protective antigen-specific IgG antibodies. In a preferred embodiment, the conjugated label pad comprises Protein A conjugated with colloidal gold.

In a preferred embodiment, the sample is placed on a sample pad, the sample filters down through the sample pad and then through a conjugate label pad containing a conjugate label, e.g., Protein A conjugated with colloidal gold. The gold particles serve as an indicator dye. The conjugate label binds to IgG antibodies in the sample to form a complex, and the complex then migrates along the membrane or detection strip. PA-specific antibodies bind to the recombinant PA antigen that is immobilized in a discreet location on the membrane. Formation of this double antigen-antibody complex causes the indicator dye to precipitate and form a detectable colored line, indicating a positive result that PA-specific antibodies are present in the sample. The time for this test is about 5–10 minutes, and under 20 minutes.

The results can be used to evaluate immunization status of a patient. For example, if the sample tests positive, and the sample came from a person who has received an anthrax vaccine, then the positive result will indicate that the appropriate immune response was elicited from that person, particularly if there are no other indications or symptoms of anthrax in the person. If the sample tests negative, and the sample came from a person who has received an anthrax vaccine, then the negative result will indicate that the person has not been properly immunized.

Thus, the immunoassays of the present invention provide markers of vaccine effectiveness by detecting specific IgG protective antibodies in patient bodily fluids, such as saliva. The present invention includes in vitro immunological techniques of antibody detection to validate the test by analyses of serum and saliva samples in a population of immunized military personnel. This approach has widespread future potential for monitoring exposure to toxins or disease and for assessing immunization status against various infectious diseases, including anthrax. Possible long-term applications of this hand-held, diagnostic tool include continuing field surveillance of vaccinated personnel to verify protective immunization and to assist in the determination of the optimum dose schedule for anthrax vaccine administrations. This test method may also be employed to monitor personnel and to follow the progression of other infectious diseases for which specific antibodies are known.

The present invention is particularly useful as a rapid, non-invasive diagnostic tool to assess anthrax immunization status of military personnel. The hand-held, in vitro test method of the present invention is designed for field use in forward-deployed areas that can be administered by minimally trained personnel. The present invention provides an immunoassay that will serve as a marker of vaccine effectiveness to assess the level of protective antibodies. Applications of this test method may also provide useful data to determine the optimum number of doses and schedule for anthrax vaccinations ("Anthrax Vaccine Adsorbed (AVA)"). This could be accomplished by following the progression of antibody response at each stage of the AVA vaccination series. By monitoring antibody titer, it can be determined: (1) If the current six injection series is needed for vaccine effectiveness; (2) If annual boosters are required to maintain protective immunization, or alternatively, how long anthrax immunization lasts; and (3) The point in the injection series at which maximum antibody titer is achieved. It is not possible to conduct research to directly determine patient vaccine effectiveness against the inhalation form of anthrax. However, protection of non-patient primates with the AVA vaccine has been demonstrated in a number of laboratories and continues to provide the best supportive evidence of its efficacy.

The present invention can also be used to verify the exposure to a biowarfare agent, such as anthrax, in a patient. For example, if the sample testing positive came from a patient who has not been vaccinated against the biowarfare agent, then the positive test indicates exposure to the biowarfare agent in the patient, and treatment against the biowarfare agent should begin immediately. Detection of Immunoglobulin M (IgM) or other immunoglobulins (other than IgG) may be more appropriate in this use and certain other uses.

BRIEF DESCRIPTION OF THE DRAWINGS

FIG. 1 shows a top view of a preferred embodiment of the present invention.

FIG. 2 shows a side view of the preferred embodiment shown in FIG. 1.

DETAILED DESCRIPTION OF THE INVENTION

As shown in FIGS. 1 and 2, a preferred immunoassay 10 of the present invention, comprises a sample well 12, a sample pad 14, a conjugate label pad 16, a membrane or detection strip 18, an absorbent pad 20, an adhesive layer 22, a plastic backing 24, and a plastic housing 40. Sample pad 14 overlaps with conjugate label pad 16 to form a first overlap zone 26. Conjugate label pad 16 and membrane 18 form a second overlay zone 28. Membrane 18 and Absorbent pad 20 form a third overlap zone 30. A sample (not shown) can be placed in sample well 12 and filters down through the sample pad 14 and then through a conjugate label pad 16 containing a conjugate label, e.g., Protein A conjugated with colloidal gold. The gold particles, preferably about 45 nm in size, serve as an indicator dye. The conjugate label binds to IgG antibodies in the sample to form a complex, and the complex then migrates along the membrane 18.

Figure 2:
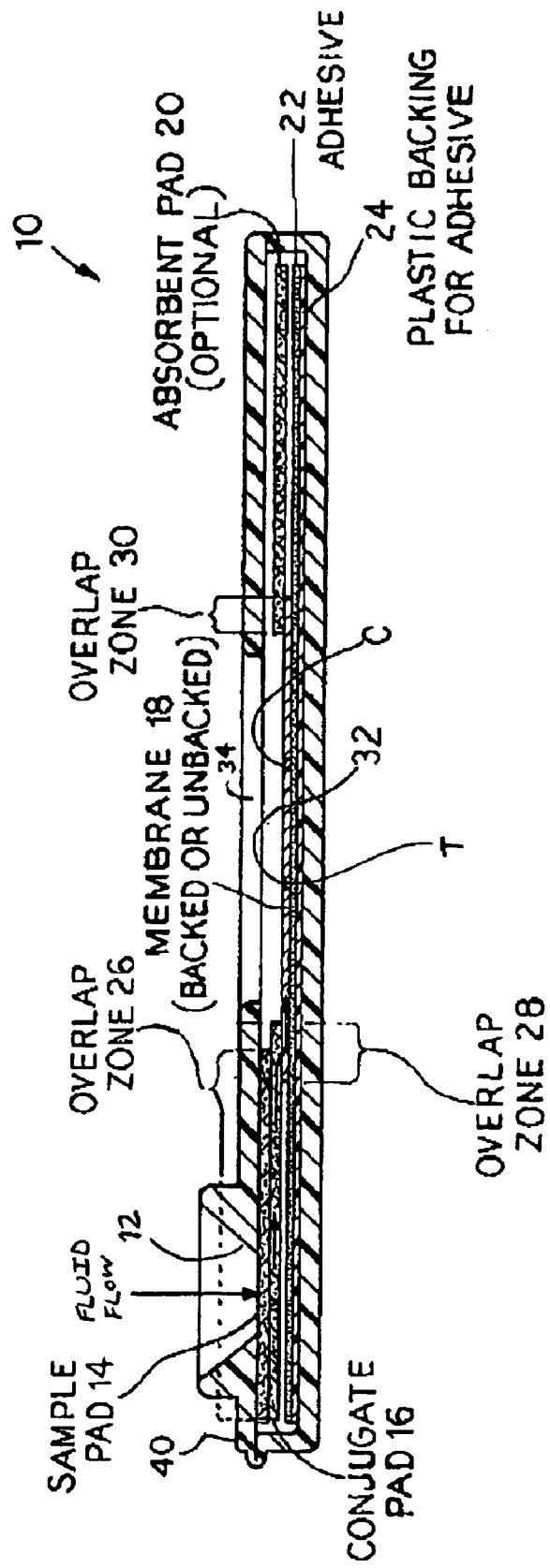

Anthrax PA-specific antibodies bind to the recombinant PA antigen that is immobilized in a discreet location 32 on membrane 18. Formation of this double antigen-antibody complex causes the indicator dye to precipitate and form a detectable colored red line (illustrated as "T" in FIG. 1), indicating a positive result that anthrax PA-specific antibodies are present in the sample. FIG. 2 is an illustration of a test strip from Millipore Corporation (see Mansfield, M. (1999) A Short Guide: Developing Immunochromatographic Test Strips, Millipore Corporation, Bedford, Mass.) that has been modified in accordance with the present invention.

An assay is recorded as positive when a distinct band of the PA antigen (T on the assay 10 in FIG. 1) appears in addition to the control band. A Protein A control line will also form whether the PA antigen line is visible or not, indicating the test is functioning properly. A negative test results when only the control (C) band appears in the membrane window. Preferably, each lateral-flow device is individually packaged in a plastic-lined foil pouch with a desiccant pad to ensure stability. These testing devices can be stored long-term at room temperature with no loss of activity.

The testing devices comprise 0.72 and 1.8 $\mu$g rPA protein immobilized on nitrocellulose strips as the test indicator (T) and Protein A as the control band (C). The amount of membrane-bound antigen is important. It is necessary to have excess binding capacity to capture all of the desired IgG, yet not too great to cause diffusion and band broadening. Experience with saliva sample testing has shown that 4 drops, as added by bulb-pipette, work best for obtaining optimum results. This amount provides sufficient testing volume, and subsequent capillary flow pressure, to ensure optimum membrane flow rate as the sample migrates the entire length of the membrane. Calibration of several plastic, bulb-pipette medicine droppers that are used to add sample to the device indicates that each drop consists of about 40 $\mu$L volume. Therefore 4 drops or 160 $\mu$L sample volume will be used for each test. Four drops of unstimulated saliva followed by 3 drops of saliva dilution buffer as chase solution also appears to facilitate sample flow by breaking up the mucins.

Test results using PBS serial dilutions spiked with Goat anti-AVA IgG1 polyclonal antibody (BioPort, Corporation) showed a positive result for PA-specific IgG antibodies at dilutions ranging from 1:250 through 1:32,000 (v/v). This indicates that the testing device and method described above will specifically detect anti-PA IgG antibodies with a sensitivity of at least 5 ng protein. Saliva specimens that are undiluted and diluted 1:1 to 5:1 (saliva:buffer, v/v) with Phosphate-Buffered Saline (PBS) containing 10 mM ethylenediamine tetraacetic acid (EDTA) and 0.1% sodium azide were tested to study sample viscosity due to mucin content and methods to overcome testing difficulties. Saliva dilutions up to 5 parts saliva to one part buffer show marked improvement in membrane flow properties and produce a clear signal at the Protein A control line.

The time for this test is about 5–10 minutes, and under 20 minutes. The results can be used to evaluate immunization status of a patient. For example if the sample came from a person who has received an anthrax vaccine, then the positive result will indicate that the appropriate immune response was elicited from that person, particularly if there are no other indications or symptoms of anthrax in the person. If the sample tests negative, and the sample came from a person who has received an anthrax vaccine, then the negative result will indicate that the person has not been properly immunized.

If the sample tests positive, and the sample came from a person who has not received an anthrax vaccine, then the positive result will indicate that the person has been exposed to anthrax, and treatment against anthrax should begin immediately. If the sample tests negative, and the sample came from a person who has not received an anthrax vaccine, then the negative result will indicate that the person has not been exposed to anthrax, particularly if there are no other indications or symptoms of anthrax in the patient.

Membrane 18 can comprise any suitable material, e.g., a uniform-sized (10×500 mm) nitrocellulose membrane (Millipore™ XA3J072100). Conjugate label pad 16 can contain any suitable marker, e.g., dried colloidal gold-labeled Protein A as marker (see FIGS. 1 and 2) and be placed at one end of membrane 18. An absorption pad 20 is located at the opposite end of the membrane 18 and serves to draw the sample, e.g., saliva, along the membrane 18 by capillary action. A plastic backing 24 provides support for the adhesive layer 22 and membrane 18, and the combination can be cut into individual test strips (e.g., 5×60 mm) and fitted into a plastic housing. A round sample application well 12 is positioned directly above the sample pad 14, and a rectangular detection window 34 is located above the nitrocellulose membrane 18.

The objectives of the present invention include the following:

1. Develop a rapid, in vitro method to detect anthrax anti-PA antibodies in whole saliva and/or oral fluid including oral mucosal transudate and gingival crevicular fluid.
2. Optimize reaction conditions to enhance limits of detection, including sample preparation, preventing proteolysis, antigen form and secondary antibody conjugates to amplify the visual signal.
3. Determine assay sensitivity and specificity and refine test method parameters.
4. Evaluate assay performance for detection of anthrax anti-PA antibodies in comparison to Enzyme-Linked Immunosorbent Assay (ELISA) in a small group of immunized military personnel, with final assay refinement.
5. Conduct parallel serum and saliva ELISA assays in a large subject population to validate the test method.
6. Analyze data to determine if saliva and/or oral fluid including oral mucosal transudate and gingival crevicular fluid is a viable substitute for serum in immunoassays to evaluate anthrax immune status, and prepare lateral flow device for distribution.

Salivar Diagnostic Procedures

A significant strength of this proposal is that rapid diagnostics have now attained sufficient sensitivity to offer a compact, in vitro test method as a viable alternative to instrumental assays. In fact a number of immunochromatographic tests are now commercially available to confirm presence of a variety of infectious diseases, drugs of abuse, allergies and sexually transmitted diseases among others. Mansfield, M. (1999) *A Short Guide: Developing Immuno-*

*chromatographic Test Strips*, Millipore Corporation, Bedford, Mass.

Although these assays employ serum or urine as the tested body fluids, in accordance with the present invention, oral body fluids can be used. Saliva antibody content mirrors that in serum.

Saliva Samples

Saliva consists of over 99% water with less than 1% solid constituents including albumins, globulins, enzymes and mucins. Salivary mucin is a high molecular weight glycoprotein and is principally responsible for the viscous, lubricating nature of the fluid. Saliva has not been as rigorously studied as other body fluids, and data characterizing salivary antibody makeup and concentration are not as common as for serum. However, it is known that saliva contains the same antibody classes as serum in lower, but measurable quantities. Based on the available literature, it is expected that about a 900-fold lower IgG level is in whole saliva compared with that in serum. Total IgG levels in serum have been reported as 1250 mg/100 mL, while that for whole saliva is 1.4 mg/100 mL. Roitt, I. M., and Lehner, T. (1980) Chapter 11: Oral Immunity. In *Immunology of Oral Diseases* p. 307, Blackwell Scientific Publications, Boston, Mass.

In an average saliva sample of 5 mL, 0.07 mg or 70 $\mu$g IgG would be present. To enhance detection, assay amplification procedures can be studied to improve the ability to measure specific salivary IgG antibodies. Serum and saliva ELISA analyses of anti-PA specific and total IgG will allow for normalization of saliva values and obtain comparative data.

Saliva contains only a trace of, if any, protease enzymes as the bulk of protein digestion begins in the stomach. However, bacteria present in saliva can secrete proteases with some degradative effect on salivary proteins. See Orten, J. M., and Neuhaus, O. W. (1975) Chapter 13: Nutrition: Digestion, absorption, and energy metabolism. In *Patient Biochemistry* pp. 442–443, The C. V. Mosby Company, St. Louis, Mo.

The protease effect on salivary antibodies can be studied and a protease inhibitor additive can be developed to counteract this potential degradation.

As previously noted, the possible threat of personnel exposure to biological warfare agents and the protection of United States Armed Forces in this event has been a primary concern for the Department of Defense. The inexpensiveness, accessibility and relative ease of handling anthrax bacteria make this an especially troublesome weapon and a relevant threat to military personnel. Anthrax immunizations are required for deployed service members and are an important component of our integrated force health protection program. The present invention provides a method and device to preserve and maintain the health of United States military personnel in support of military operations. Another aspect of the present invention is to help monitor a vaccination program and provide methods and devices to monitor vaccine effectiveness. The present invention provides a test method to quickly assess vaccine efficacy and measure antibody response over the course of the vaccination senes.

The in vitro salivary diagnostic test of the present invention provides a significant step forward in field-test capability and in making rapid assessment of immune status, including such assessment at remote-site operations. The present invention can be used as a screening test for all immunized military personnel and provide clinicians with a valuable diagnostic tool to monitor anthrax vaccination progress.

This salivary diagnostic tool also offers a considerable range of options for verification of vaccine effectiveness, confirming exposure to a number of infectious diseases, and tracking disease progression by monitoring individual antigen level and antibody response. These applications are possible when a specific antigen of the disease and its corresponding antibody are known.

EXAMPLE 1

General:

The design and rationale for this study rest on the importance of using saliva as the test medium to measure anthrax vaccine effectiveness. This rapid immunoassay avoids venipuncture and the necessity of having trained corpsmen to collect samples for measurement of anti-PA antibodies. Sample collection is non-invasive with no perceivable discomfort or risk to the individual. A positive confirmation of anthrax antibodies is readily observed within 5–10 minutes by the appearance of the test band. The assay is straightforward with no other chemicals or reagents needed to perform the test.

The following sections describe the experimental approach designed to address three specific aims: (1) To optimize the assay of the present invention by signal amplification methods to achieve the most sensitive results; (2) To determine assay specificity by studying false positive and false negative results in the small pilot study; and (3) To validate the assay with parallel serum and saliva ELISA measures of antibody levels in a large subject population.

Determining Assay Sensitivity and Specificity

Assay sensitivity can be developed by testing serial dilutions of commercially available anti-PA and anti-AVA antibodies with the lateral-flow device of the present invention. Antibody standards can be prepared in saliva and in buffered saline to study the possibility of mucin interference with the assay. Antigen selection and antibody detection methods are critical to maximize assay sensitivity and specificity as indicated by a colorimetric marker. Factors investigated for optimization of assay conditions include sample preparation, antigen form, various conjugated secondary antibody markers to amplify detection and methods to facilitate antibody capture by membrane-bound antigen.

Testing and evaluation can lead to a determination of assay specificity to reduce false positive and false negative responses from a range of prepared standards. Positive and negative specimen results in the rapid test method can be compared with results of ELISA for identical samples. ELISA test conditions can be optimized for saliva using appropriate antigen and antibody detection systems to give enhanced responses for specific and total IgG. Based on these results, various aspects of the assay can be refined.

A testing protocol can be developed, including large-scale specimen collection and testing at an established anthrax immunization program site.

In a further phase in the development of the present invention, serum and saliva samples can be collected from a large number of military personnel and tested in parallel ELISA studies to compare antibody titers and to validate the salivary diagnostic method with quantitative and statistically supported data.

The sensitivity and specificity of the assay of the present invention can be evaluated by making serial dilutions of a solution spiked with available polyclonal IgG antibodies specific for PA toxin protein. BioPort Corporation's Goat anti-AVA IgG1, 4.3 mg/mL in 50 mM 4-(2-hydroxyethyl)-

1-piperazineethanesulfonic acid (HEPES) buffer, pH 7.0, can be made to 1 µg/µL concentration in PBS. Serial dilutions of this polyclonal antibody can be prepared in PBS, pH 7.4, at dilutions ranging from 1:250 to 1:64,000. Each dilution can be prepared by taking a 1 mL aliquot of the previous solution and diluting 1:1 with fresh PBS. The complete progression of antibody dilutions can be 1:250, 1:500, 1:1000, 1:2000, 1:4000, 1:8000, 1:16,000, 1:32,000 and 1:64,000. These dilutions can be tested with the assay 10 of the present invention to verify positive reaction results for PA-specific antibodies at least through 1:16,000, or about 10 ng protein, and evaluated for dose-response reactions in the indicator test line. Test results indicated detection of Goat anti-AVA IgG1 antibody to less than 5 ng.

The same dilutions of Goat anti-AVA IgG1 antibody can be made in saliva to test whether mucin interferes with the assay. Dilutions of 1:500, 1:2000 and 1:8000 can also be made by adding the appropriate amount of antibody to saliva that is already diluted 1:1 with PBS containing 10 mM EDTA and 0.1% sodium azide. From the initial 1:500 standard, subsequent 1:4 dilutions of each saliva solution can be made with PBS. The EDTA has been shown to minimize mucin viscosity and thereby facilitate saliva testing. This example confirmed that the EDTA buffer does not affect the specific IgG antibody nor does it interfere with antigen-antibody binding.

Also, in duplicate solutions of these same three saliva antibody dilutions, 1:500, 1:2000 and 1:8000, Sigma™ Protease Inhibitor Cocktail can be added 1:20 immediately after the solution is made and tested against the spiked saliva sample with no protease inhibitor. These side-by-side samples can be tested at +15 minutes, 60 minutes, 3 hours and the following day to examine any possible degradation effects of oral bacterial enzymes on the anti-PA antibody.

These solutions can be tested with the diagnostic assay and ELISA to 1) identify limits of detection and 2) develop a quantitative standard curve in which dose-response relationships from the ELISA assays can be used to evaluate the assay method.

Antigen/Antibody Detection

A goal of the present invention is to assess anthrax vaccine immune status. Protective antigen is the antigen of choice for assay development, supported by a large body of literature indicating it is the antigenic component of the anthrax toxin. For anthrax, the entire antigen-antibody specificity issue then distills down to a single protein and the IgG antibodies made against PA, the main component of the AVA vaccine. Also, various techniques have been employed in other laboratories to enhance expression of PA and thereby increase the relative antibody titer produced against it.

Techniques to amplify visual detection of antigen-antibody binding can be investigated. Preparation of a dendrimer or polymer tree, immobilized on the nitrocellulose with PA protein or reactive peptides bound to branches, may increase accessibility of the antigen and enhance antibody capture. Another method of signal amplification to study is using different secondary antibody-conjugate detection systems to find the most sensitive procedure for this assay. An example of one conjugate label is Protein A conjugated with colloidal gold to provide a visual detection of specific antibody binding. However, if necessary, the enzymes alkaline phosphatase, horseradish peroxidase and biotin-Streptavidin conjugated to a secondary antibody may be used to offer more sensitive probes that will enhance the detection of antigen-antibody complex formation.

False positive and false negative tests can be studied to determine specificity of the assay. This determination can be made using salivary standards of known dilutions of Goat anti-AVA antibody and samples collected from subject volunteers in the pilot study (to ensure a sufficient number of both positive and negative trials). Reproducibility of test results for these salivary standards and samples will determine the rate of false positives or negatives. Results using the immunoassay method and kit of the present invention can be compared with ELISA values obtained for the same samples or specimens. Specificity determinations can be conducted with 3 repetitions of each standard or sample and ELISA comparative analysis. A false negative is defined as a test that only shows the control (C) band when other assay test repetitions of this same sample indicate positive with both the control and test bands clearly visible. A false negative determination can be supported by positive ELISA results of this same sample indicating the presence of anti-PA antibody above negative control values. Conversely, a false positive is defined as visual detection of both test and control bands, but further test repetitions of this sample indicate negative and/or ELISA results for this sample are less than those obtained from the lowest detectable anti-PA antibody dilution.

Preliminary specificity studies were initiated with saliva samples collected from five study volunteers, A, B, C, D, and E. Three of the five volunteers, A, B, and C, had not received any of the AVA series, and the saliva samples from these three volunteers all tested negative for anthrax IgG antibodies using the assay of the present invention. Thus, the present invention confirmed that these three volunteers had not been immunized for anthrax. The other two volunteers, D and E, had received at least one of the AVA series. Volunteer D had received 4 of the AVA series with the last injection occurring about 36 months prior to the test. The saliva sample from Volunteer D tested negative for anthrax IgG antibodies using the assay of the present invention. Volunteer E had received three of the AVA series, with the last injection occurring about 19 months prior to the test. The saliva sample for Volunteer E indicated a positive test in two different dilutions of saliva with dilution buffer. However, when this test was repeated 1½–2 hours later, the same diluted saliva sample, and a second dilution made in fresh dilution buffer, indicated negative. Although the saliva sample from Volunteer E was placed on ice immediately after collection, it was concluded that protease activity of the saliva may have degraded the anti-PA antibody in the 1–2 hour interim between the first and second test. Further tests can be conducted by adding Signa™ Protease Inhibitor Cocktail 1:10 or 1:20 to saliva samples just after collection and the test repeated for the same individual. ELISA analysis can also be performed for these saliva samples to verify antibody presence. It is also possible to use stimulated saliva samples in which protease activity, if present, should be minimized during collection (as described below).

Sample Collection

Saliva samples can be collected from study volunteers in three ways: Volunteers initially can provide unstimulated saliva by allowing available saliva to drip into a small polypropylene collection cup over 3–5 minutes. According to a preferred embodiment a polypropylene collection cup or container may be used. It is within the scope of the invention to use a pliable material for the container as described in column three of U.S. Pat. No. 5,922,614, which is expressly incorporated herein by reference thereto. Volunteers can be given a single piece of sugarless peppermint chewing gum and asked to chew for 30 seconds before collecting samples of stimulated saliva. Typically, volunteer subjects provide sample volumes of about 2–4 mL for unstimulated saliva, while a volume of 5–8 mL is most common after chewing a piece of gum. Alternatively, an absorbent element may be rubbed along the gum line for a short period of time, preferably up to thirty seconds, then the absorbent element may be held in place along the gums for a longer period of time, preferably up to two minutes. U.S. Pat. No. 5,830,410, which is expressly incorporated herein by reference thereto, more fully describes this method in columns six and seven and also describes a representative collection device in FIGS. 1A and 1B. The pliable material collection cup or container may be placed around the oral-fluid-saturated absorbent element and deformed or squeezed to extract the oral fluid. Each of these samples can be placed on ice immediately after collection to ensure stability.

To preserve saliva samples for storage and biological assay in accordance with the present invention, a mycobacteriocidal protease inhibitor solution may sometimes be appropriate.

For example, a general protease inhibitor cocktail (premade Sigma™ Protease Inhibitor Cocktail P2714) can be added to each sample 1:20 to prevent protein degradation from oral bacterial enzymes. These samples can then be returned to the laboratory for testing.

A protease inhibitor cocktail can be provided as 100× lyophilized powder. The protease inhibitor cocktail can be reconstituted to 10× with Barnstead Still quality water [10 ml].

TABLE of WORKING CONCENTRATIONS in Protease Inhibitor Solution
  EDTA 10 mM
  AEBSF 20 mM
  Bestatin 1300 $\mu$M
  E-64 14 $\mu$M
  Leupeptin 10 $\mu$M
  Aprotinin 3 $\mu$M At these working concentrations, the protease inhibitor solution can be diluted 10× for proteolytic inhibition.

Saliva specimens can be tested immediately for presence of anti-PA antibodies. Samples can then be placed into graduated conical tubes, their volume recorded, and finally placed into frozen storage at −80° C. to await ELISA comparative testing for anti-PA IgG determinations.

Serum and saliva specimens can be collected from a large population of volunteers (Phase II of the study) at distant clinics or medical treatment facilities with an established anthrax vaccination program. Collection of these test samples can be in cooperation with trained medical personnel. Saliva samples can be collected in small polypropylene collection cups as previously described, and transferred into graduated, conical plastic tubes for frozen storage and shipment. The tubes provided for saliva shipment can have protease inhibitor preweighed into each tube to give about a 1:20 concentration in an average sample volume of 5 mL. Blood samples can be drawn by trained corpsmen or other medical staff, centrifuged to precipitate red blood cells, and the supernatant collected in graduated tubes for immediate frozen storage. Only sequential sample numbers will identify collected samples, with volunteers' social security numbers and other pertinent data recorded in the database of study participants. In accordance with the Protection of Patient Subjects testing protocol, all personal identifying information will be destroyed at the conclusion of the study.

Assay lateral flow of the present invention and ELISA assays can be performed with serum and saliva samples in a double-blind controlled study so that the results of the two assays with each sample type may not be matched against each other until the data are collated and analyzed.

Comparison with ELISA

The present standard for measuring antibody titer is ELISA, a very reliable, but relatively time-consuming and labor-intensive process. Highly trained laboratory personnel usually perform these determinations, and the instrumentation required is relatively sophisticated and expensive. While ELISA has been the laboratory standard for measuring antibody response, it is more problematic to perform this diagnostic test in forward-deployed regions where personnel are at greater potential risk for anthrax toxin exposure. Development of a rapid, economical test procedure that can be performed by minimally trained personnel will provide a field test option to verify protective immunization.

Serum ELISA procedures are well established in the literature and in this laboratory. Procedures for saliva ELISA analyses must be developed and optimized for anti-PA IgG antibody detection. Saliva testing procedures previously conducted in this laboratory involve saliva samples diluted 1:5 with 1/10× saliva dilution buffer (PBS with 10 mM EDTA and 0.1% azide). About 350 ng sample of rPA, (reported binding capacity of Immulon 4 microtiter plates), can be used to coat the 96-well polystyrene plates (Immulon 4, Dynatech™ Incorporated), which are incubated for 1 hour at 37° C., followed by blocking with 1% Bovine Serum Albumin (BSA) and 0.5% Tween 20TM in PBS. Specific IgG anti-PA antibody derived from a saliva sample diluted 1:5 with 1/10× saliva dilution buffer can be incubated with the antigen at 37° C. for a minimum of 60 minutes. The plate can be developed with Goat anti-Patient IgG1 (estimated 1:500 dilution) secondary antibody conjugated with alkaline phosphatase for substrate detection.

Preparation of Recombinant Protective Antigen

A sample of 85% purified recombinant PA in Tris buffer (Tris (hydroxymethyl)aminomethane) was provided by BioPort Corporation, Lansing, Mich., manufacturer of the U.S. anthrax vaccine. Briefly, the recombinant protein is made by transforming avirulent *Bacillus anthracis* BH441 cells ($PXO1^-$ and $pXO2^-$) with a PA expression vector containing the pag gene. This shuttle vector then directs recombinant PA antigen over-expression using the replicating mechanisms of *Escherichia coli* host bacteria. The recombinant protein is purified from the culture supernatant using Phenyl Sepharose, a hydrophobic interaction column, followed by Q Sepharose, anion-exchange chromatography. The final product is then dialyzed into Tris buffer at pH 7.2. Upon receipt, the purity of the rPA protein (83 kDa) was verified by gel electrophoresis and immunoblotting with monoclonal anti-PA IgG1 and polyclonal anti-AVA IgG1 antibodies.

Protection of Patient Subjects (PHS) Testing Protocol

A PHS study protocol has been written and submitted for approval by the command Institutional Review Board (IRB) to obtain authorization to recruit volunteer subjects for the pilot study. In accordance with this protocol, local area active duty personnel and reservists who have had at least one of the AVA injections can be recruited for participation in Phase I according to the procedures outlined in the PHS protocol. Potential study volunteers can be contacted through the Naval Hospital Great Lakes Immunization Clinic, the Naval Reserve Center, Great Lakes, and the Armed Forces Dental Research Facility, Great Lakes. Also, a brief notice of the study and request for volunteers can be published in general health and fitness mailings to area active duty and reserve personnel, and in the Naval Training Center, Great Lakes Bulletin, a weekly base newspaper. The local immunization clinic begins the AVA vaccine series for personnel who have received orders for deployment to foreign areas considered to be at greatest risk for possible anthrax exposure.

Phase I of the salivary diagnostic study has received approval from the IRB, guided by appropriate Federal regulations at 45 CFR 46 and other requirements governing the use of patient subjects in research protocols. At least one study assistant can review the testing procedures and purpose of the study with individual volunteers, obtain signed permission to collect a sample on an Informed Consent Form, and obtain authorization to take personal data as it relates directly to the study in a signed Privacy Act Statement. As testing progresses for the pilot study, a PHS protocol can be written and submitted for review by the command IRB and the review committee of our collaborating laboratory(ies) to obtain authorization to recruit volunteer subjects for Phase II of this study.

Study volunteers can be asked how many of the six AVA injections they have received and how long it has been since their last immunization. This information will be recorded in the subject database to compare with observed results. Study volunteers can be grouped, if possible, based upon the number of AVA injections they have completed. Individual medical records can be reviewed only to confirm self-declared immunization history and any medical conditions that could potentially impact the outcome of the diagnostic test.

Data Statistical Analyses

A statistician can consult with the Principal Investigator on experimental design to ensure appropriate open and blind controls are incorporated into the study. The mechanisms of the assay system can be developed so that the assay can provide sensitivity and specificity of at least 90% based on final tests of 150 negative and 150 positive samples. Using serum and saliva samples from subjects with and without AVA immunizations, the saliva test method can be optimized so that, compared to gold-standard serum methods (ELISA), the assay of the present invention can have sensitivity and specificity of at least 80% that of serum methods using 90% one-tailed confidence limits.

Additional Preliminary Findings

Peptide Mapping

Some preliminary work has been done with PA peptide fragments that may form some of the antigenic sites within the 735 amino acid toxin (excluding the 29 amino acid N-terminal signal sequence that is cleaved upon activation). Specific peptide fragments were selected for study based on demonstrated antigenic reactions to anti-PA antibodies in the literature and on very hydrophilic values obtained through application of the data to the Hopp-Woods plot. Hopp, T. P., and Woods, K. R. (1981) Prediction of protein antigenic determinants from amino acid sequences. *Proc Natl Acad Sci USA* 78, 3824–3828.

Little and others described antigenic reactions of a series of polyclonal and monoclonal antibodies to three specific PA amino acid sequences: (1) in the furin-sensitive (protease) region; (2) the EF/LF factor binding region; and (3) the C-terminal membrane-binding domain. Little, S. F., Novak, J. M., Lowe, J. R., Leppla, S. H., Singh, Y., Klimpel, K. R., Lidgerding, B. C., and Friedlander, A. M. (1996) Characterization of lethal factor binding and cell receptor binding domains of protective antigen of *Bacillus anthracis* using monoclonal antibodies. *Microbiology* 142, 707–715. Antibody binding to each of these antigenic regions neutralized toxin activity by preventing PA activation or membrane recognition and binding of PA to the host cell.

The rationale for using small peptide fragments is that it may be possible to better define the antigenic sites of PA critical to anthrax toxicity. A more complete understanding of PA binding domains and formation of the antigen-antibody complex will help elucidate mechanisms of toxin action and its inhibition.

In preliminary findings, five PA peptide fragments of 3000 approximate mass have been identified that may have antigenic activity to anti-PA antibodies. Of these peptides, two have proven to be antigenic by Dot Blot procedures. These active fragments are: a 26-mer of amino acids #576–601 that is a part of the EF/LF binding site of PA; and a 29-mer, amino acids #707–735 at the C-terminal end where the cell membrane receptor recognition and binding site is located. Further study may further define the binding properties of these synthetic antigenic reaction sites.

The term patient used herein includes humans, as well as animals. Thus, the present invention can be used for diagnostics for veterinary tests.

Obviously, many modifications and variations of the present invention are possible in light of the above teaching. It is therefore to be understood that, within the scope of the appended claims, the invention may be practiced otherwise than as specifically described. The principles described above can be readily modified or adapted for various applications without departing from the generic concept, and therefore such adaptations and modifications are intended to be comprehended within the meaning and range of equivalents of the enclosed embodiments. It is to be understood that the terminology and phraseology herein is for the purpose of description and not of limitation.

We claim:

1. A method for detecting the presence of an antibody to *Bacillus anthracis* antigen, the antibody present in a sample selected from one or more patient bodily fluids which comprises the following steps: (a) contacting the sample with a conjugate label comprising a label conjugated to a binding partner for the antibody in the sample a, thereby forming an antibody-conjugated label complex; and (b) allowing the antibody-conjugated label complex to migrate along a lateral-flow assay membrane and contact at least one membrane-bound recombinant *Bacillus anthracis* protective antigen, thereby forming an antigen-antibody complex and causing the indicator dye to precipitate and form a detectable signal, whereby the presence of the antibody is determined in the sample by an intensity or presence of the signal.

2. The method of claim 1, wherein the one or more patient bodily fluids is selected from the group consisting of saliva, oral rinse expectorant, oral fluid including oral mucosal transudate and gingival crevicular fluid, urine, sweat, tears, blood, serum, stool, gastric fluid, synovial fluid, and phlegm.

3. The method of claim 1, wherein the one or more bodily fluids is saliva.

4. The method of claim 1, further comprising the step of evaluating immunization status of the patient from whom the sample came by comparing the signal or lack thereof with immunizations or lack thereof previously received by the patient.

5. The method of claim 1, wherein the recombinant at *Bacillus anthracis* protective antigen specifically binds to *Bacillus anthracis* protective antigen-specific IgG antibodies.

6. An immunoassay kit for detecting, a predesignated, target IgG antibody in a sample selected from one or more patient bodily fluids which comprises:
(a) a sample pad,
(b) a conjugated label pad having a conjugated label comprising a label conjugated to a binding partner for the antibody in the sample, a portion of the conjugated label pad and a portion of the sample pad forming, first interface, (c) a lateral flow membrane, wherein a portion of the membrane and a portion of the conjugated label pad forming a second interface, and (d) a recombinant *Bacillus anthracis* protective antigen bound to the membrane, the first interface allowing fluid to flow from the sample pad to the conjugated label pad and contact the indicator dye wherein the antibody present in the sample forms an antibody-conjugated label complex, the second interface allowing fluid to flow from the conjugated label pad to the membrane and to contact the at least one membrane-bound recombinant *Bacillus anthracis* protective antigen to form to in antigen-antibody complex and cause the indicator dye to precipitate and form a detectable signal.

7. The immunoassay kit of claim 6, wherein the recombinant *Bacillus anthracis* protective antigen specifically binds to *Bacillus anthracis* protective antigen-specific IgG antibodies.

8. The immunoassay kit of claim 6, wherein the binding partner comprises Protein A.

9. The immunoassay kit of claim 8, wherein the label is colloidal gold.

* * * * *